(12) United States Patent
Spartiotis et al.

(10) Patent No.: US 9,310,495 B2
(45) Date of Patent: Apr. 12, 2016

(54) PHOTON/ENERGY IDENTIFYING X-RAY AND GAMMA RAY IMAGING DEVICE ("PID") WITH A TWO DIMENSIONAL ARRAY OF PIXELS AND SYSTEM THEREFROM

(75) Inventors: Konstantinos Spartiotis, Espoo (FI); Tuomas Pantsar, Espoo (FI); Charalampos Lampropoulos, Espoo (FI); Theofanis Orfanoudakis, Espoo (FI)

(73) Assignee: OY AJAT LTD., Espoo (FI)

( * ) Notice: Subject to any disclaimer, the term of this patent is extended or adjusted under 35 U.S.C. 154(b) by 483 days.

(21) Appl. No.: 13/342,277

(22) Filed: Jan. 3, 2012

(65) Prior Publication Data

US 2012/0280131 A1  Nov. 8, 2012

Related U.S. Application Data

(60) Provisional application No. 61/482,381, filed on May 4, 2011.

(51) Int. Cl.

| | |
|---|---|
| *G01T 1/29* | (2006.01) |
| *G01T 1/24* | (2006.01) |
| *H04N 5/32* | (2006.01) |
| *H04N 5/347* | (2011.01) |
| *H04N 5/3745* | (2011.01) |

(Continued)

(52) U.S. Cl.
CPC *G01T 1/247* (2013.01); *H04N 5/32* (2013.01); *H04N 5/347* (2013.01); *H04N 5/378* (2013.01); *H04N 5/3745* (2013.01); *A61B 6/4241* (2013.01); *G01T 1/2928* (2013.01)

(58) Field of Classification Search
CPC .......... G01T 1/47; G01T 1/2928; H04N 5/32; A61B 6/4241
USPC ........................................ 250/336.1
See application file for complete search history.

(56) References Cited

U.S. PATENT DOCUMENTS 5,315,631 A    5/1994 Hillen et al.
5,629,524 A *  5/1997 Stettner et al. ........... 250/370.09

(Continued)

FOREIGN PATENT DOCUMENTS

EP       0558117 A2    9/1993
WO    2004071299 A1    8/2004

(Continued)

OTHER PUBLICATIONS

International Search Report, dated Nov. 26, 2012, from corresponding PCT application.

*Primary Examiner* — Christine Sung
(74) *Attorney, Agent, or Firm* — Young & Thompson

(57) ABSTRACT

An photon (energy) identifying radiation imaging device, for imaging x-ray, gamma ray and charged radiation in medical, dental and industrial applications. The imaging device includes a detector substrate and a readout substrate. The detector substrate has a plurality of detector pixels and the readout substrate has a plurality of corresponding pixel readout circuits. Each pixel readout circuit has circuitry for processing an input analog signal and also has one or more buffers for temporarily storing values corresponding to the signal of at least two individual incoming radiation events. The readout substrate includes a digital controller having digital processing units for carrying out off-pixel digital signal processing and data/rate reduction prior to readout.

23 Claims, 10 Drawing Sheets

(51) Int. Cl.
*H04N 5/378* (2011.01)
*A61B 6/00* (2006.01)

(56) References Cited

U.S. PATENT DOCUMENTS

| | | | |
|---|---|---|---|
| 6,248,990 | B1 | 6/2001 | Pyyhtia et al. |
| 6,355,923 | B2 | 3/2002 | Pyyhtia et al. |
| 6,384,519 | B1* | 5/2002 | Beetz et al. ............ 313/103 CM |
| 7,193,217 | B2 | 3/2007 | Heismann et al. |
| 7,361,881 | B2 | 4/2008 | Spartiotis |
| 7,605,375 | B2 | 10/2009 | Spartiotis et al. |
| 8,415,023 | B2* | 4/2013 | Chang et al. ................... 428/627 |
| 2003/0035510 | A1* | 2/2003 | Strommer .................... 378/98.8 |
| 2006/0071170 | A1* | 4/2006 | Broennimann et al. . 250/370.09 |
| 2007/0024272 | A1* | 2/2007 | Zentai ........................ 324/158.1 |
| 2007/0076109 | A1 | 4/2007 | Krymski |
| 2008/0265169 | A1 | 10/2008 | Spartiotis et al. |
| 2009/0021617 | A1* | 1/2009 | Oggier et al. ................. 348/294 |
| 2009/0050818 | A1* | 2/2009 | Eversmann et al. .......... 250/389 |
| 2010/0276598 | A1* | 11/2010 | Kirby et al. .................... 250/353 |
| 2011/0017918 | A1* | 1/2011 | Baeumer et al. ......... 250/370.11 |

FOREIGN PATENT DOCUMENTS

| | | |
|---|---|---|
| WO | 2007141388 A1 | 12/2007 |
| WO | 2009115956 A2 | 9/2009 |
| WO | 2010142848 A1 | 12/2010 |

* cited by examiner

PHOTON/ENERGY IDENTIFYING X-RAY AND GAMMA RAY IMAGING DEVICE ("PID") WITH A TWO DIMENSIONAL ARRAY OF PIXELS AND SYSTEM THEREFROM

RELATED APPLICATIONS

This application claims priority to U.S. Provisional Application 61/482,381 filed May 4, 2011.

BACKGROUND OF THE INVENTION

The current invention generally relates to the field of x-ray and gamma ray imaging and more specifically to an imaging device used for collecting photons within a certain energy range or energy bins. Most often such imaging devices are referred to as "photon counting" devices and consist of a two dimensional array of pixels, each pixel comprising a detector element produced with lithography semiconductor techniques on a monolithic detector substrate for converting x/gamma rays into an electronic signal and a circuit element connected to the detector element for counting the incident x/gamma rays within a given energy range or several energy bins, utilizing in-pixel counters (thus the expression "photon counting"), or in other words counters for counting plural photons, such counters residing on each individual pixel circuit and for each pixel of the array. The prior art approach of in-pixel counters for counting incoming x/gamma ray hits into different energy bins has some advantages and several limitations which the current invention mitigates.

DESCRIPTION OF THE RELATED ART

Currently x/gamma ray imaging is divided into two broad categories: a) charge integration and b) photon counting with in-pixel counters. In charge integration the incoming radiation hits are converted into electric charge which is then accumulated (or summed up) on each pixel into a parasitic capacitance or a charge storing capacitance in the form of an FET (Field Emission Transistor) for example. In photon counting with in-pixel counters the incoming radiation hits for each photon are converted into an electronic signal, which is then amplified with a DC or AC coupled amplifier. Typically there will be then a peak hold circuit element for "holding" the value of analog signal amplitude representative of the radiation hit energy, followed by a comparator to ensure that a signal is from a real radiation hit rather than noise. The comparator or comparators are followed by in-pixel digital counter(s). Each in-pixel counter will count the number of hits in a given energy range which corresponds to a given comparator threshold. Since each pixel carries individually one or more counters for counting the incoming x/gamma ray events the category of these imaging devices is called "photon counting". Representative examples of this type of imaging devices (i.e., category (b) "photon counting" is described in detail in the prior art that follows.

In U.S. Pat. No. 6,355,923 there is described a semiconductor imaging device including an imaging substrate comprising an array of detector cells which directly generate charge in response to incident high energy radiation, and a counting substrate containing an array of cell circuits, each detector cell being associated with at least one cell circuit from the array of cell circuits, said at least one cell circuit comprising at least one counting circuit coupled to said associated detector cell and configured to count plural radiation hits incident on said associated detector cell, wherein the counting substrate is directly connected to the imaging substrate by bump bonds.

In U.S. Pat. No. 6,248,990 there is described a semiconductor imaging device including an imaging substrate comprising an image cell array of detector cells, each detector cell corresponding to an individual pixel of said image cell array, and which directly generate charge in response to incident high energy radiation, and a counting substrate containing an array of image cell circuits, each image cell circuit being associated with a respective detector cell, said image cell circuit comprising counting circuitry coupled to said respective detector cell, and configured to count plural radiation hits incident on said respective detector cell, wherein the counting substrate is directly connected to the imaging substrate by bump-bonds In U.S. Pat. No. 7,361,881 there is described an x-ray and gamma-ray radiation energy imaging device comprising a plurality of ganged-detector pixel cells, arrayed in close proximity with each other in a laminate structure formed of a semiconductor detector substrate layer bump-bonded to a readout substrate layer, wherein a ganged-detector pixel cell further comprises a plurality of detector pixels disposed on the semiconductor detector layer, the plurality of detector pixels in electrical communication with a single pixel signal circuit disposed on the readout substrate layer, and wherein a Ratio of Correspondence between the plurality of pixel detectors and the pixel circuit in a single ganged-detector pixel cell is greater than one (>1). In this x-ray and gamma-ray radiation energy imaging device each individual of the detector pixels of the pixel array are in electrical communication with a single pixel signal counting circuit disposed on an ASIC readout substrate.

U.S. Pat. No. 7,605,375 is not a "photon counting" device in the "traditional" sense, as it describes an Application Specific Integrated Circuit for use as a readout for one of radiation detection and radiation imaging, comprising: plural pixel cells, each pixel cell arranged to receive an input of an electric charge from an output of a corresponding different imaging cell of a radiation imaging detector, each said pixel cell comprised of i) an input connection, the input connection for connecting to the output of the corresponding different imaging cell, said connection to receive the electric charge generated in response to incident radiation events on the detector; and ii) a circuit connected to said input connection, said circuit for receiving and processing the charge and selectively operable to perform two or more functionalities based on processing the charge, wherein each said circuit comprises a counter and a mode logic operatively connected said counter for setting said counter to perform, selectively, at least two of a) photon counting, b) analog to digital conversion of the one of the voltage amplitude and the current amplitude, and c) timing measurement of incident radiation events.

In addition to patented "photon counting" imaging devices with in-pixel counters described above, there has been collaborations and publications of "photon counting" imaging devices with in-pixel counters. For example at the web site of the MEDIPIX collaboration: http://medipix.web.cern.ch/MEDIPIX/. The medipix imaging device is again based on a two dimensional detector pixel array laid out on a direct conversion semiconductor detector, bump bonded to a CMOS readout ASIC and each individual detector pixel is associated to a readout pixel circuitry with each pixel circuitry having one or more in-pixel counters.

The current devices for detecting x-rays and counting them with in-pixel counters have certain advantages and limitations. A key advantage is that by having a counter on each pixel, the flux of incoming x-rays or count rate for each pixel can be high. Count rates in excess of 1 million x-rays per pixel per second have regularly been reported. In some cases count rates of 5 million x-rays per pixel per second have been reported. Another advantage is that most of these devices have one or more thresholds on each pixel and before each counter. Therefore there can be an in-pixel counter corresponding to one energy range and another in-pixel counter for another energy range and so on. In this way the background noise can be reduced significantly and different bins with different x-ray energies are created.

However certain severe limitations also exist listed here:

The energy of each photon (or the binning) is only known with accuracy corresponding to the number of thresholds or counters. Typically in x-ray imaging the pixel size is 0.1 mm (or thereabouts in the range of 0.01 mm-0.4 mm). Even with the most advanced CMOS processes, one cannot accommodate (cannot fit) more than few counters on each pixel. For example such imaging devices with in-pixel counters would typically have one to less than ten counters on each pixel. This means that the energy of each and every photon is not known accurately enough, which would be a significant advantage in imaging and multi energy applications, coloring etc.

Even a few counters/pixel increase significantly the power consumption. This in turn generates a lot of heat, which affects the performance of the CMOS and the detector which is connected to the CMOS. Energy resolution suffers and electronic noise increases. Active cooling becomes necessary increasing cost and complexity.

Digital electronics and particularly counters on each pixel are very difficult to shield from the analog (amplifier) electronics. Although such shielding techniques exist to those that exert in this field, in practical terms, such counters can couple with the analog electronics and cause noise.

SUMMARY OF THE INVENTION

The current invention reduces significantly or mitigates the drawbacks of the prior art. In accordance with the present invention there is provided for an imaging device comprising an array of imaging pixels, each pixel having an input amplifier for receiving and amplifying the electronic signal generated in response to incident single x-ray events, circuitry for reading out the single photon signal (for example voltage peak-hold value or current), circuitry for digitizing the individual x-ray event signal outside each pixel and processing such for recording its energy and displaying it for imaging selectively and according to the energy. The current invention teaches digital buffers inside each pixel for temporary storage of event/signal information and/or also a digital controller off pixel for reducing the amount of data and event rate in either time or space or both, thus rendering the readout and use of this photon identifying imaging device practical.

In accordance with one aspect of the invention there is provided an energy identifying radiation imaging device comprising: a detector substrate having an two dimensional array of radiation detector pixels for detecting incoming radiation events, a readout substrate comprising a two dimensional array of readout pixel circuits coupled to said radiation detector pixels for processing electrical signals corresponding to said incoming radiation events, and a majority of said pixel circuits further comprising a buffer for storing at least two values corresponding to the signal of at least two of the detected radiation In accordance with another aspect of the current invention there is provided a photon/energy identifying radiation imaging device comprising:
a) A detector substrate having an two dimensional array of radiation detector pixels for detecting incoming radiation events
b) A readout substrate comprising a two dimensional array of readout pixel circuits coupled to said radiation detector pixels for processing electrical signals corresponding to said incoming radiation events, characterized in that said readout substrate further comprises both of:
i) Analog to Digital Conversion stage for digitizing said signals from individual incident photon events, and
ii) a digital controller for receiving said digital signal values and further processing them prior to readout.

The digital controller contains Digital Processing Units ("DPU"), capable of reducing the amount of data either time wise, or spatial wise or both and rendering the readout sequence practical. Time wise data reduction comprises integrating (or summing) the data over a period of time, which is called a readout frame and providing the number of photons events above a certain threshold for every pixel and every frame. Spatial data reduction comprises combining M×N detector pixels to a super pixel and providing the number of incident photons for each of M×N energy bins for each super pixel.

In a preferred embodiment, the two modes of operation, i.e., i) the time wise and ii) space wise data reduction are provided simultaneously. For example, for each frame one preferably receives the number of photon events above a certain threshold for each physical (or detector pixel during the frame integration time and at the same time the M×N energy bins with the number of photon events in each energy bin for each super pixel comprising the M×N pixel grouping. Furthermore in some other embodiments some of the frames may contain only the number of photon events in each pixel above a threshold and some of the frames may contain additionally the number of photon events in each energy bin for each super pixel comprising the M×N pixel grouping.

DETAILED DESCRIPTION OF THE PREFERRED EMBODIMENTS

With reference to FIGS. 1(a), 1(b), 1(c), and 2, the invention includes a radiation imaging device 32 having a detector substrate 27 connected to the readout substrate 25 and further substrate 28.

Figure 1A:
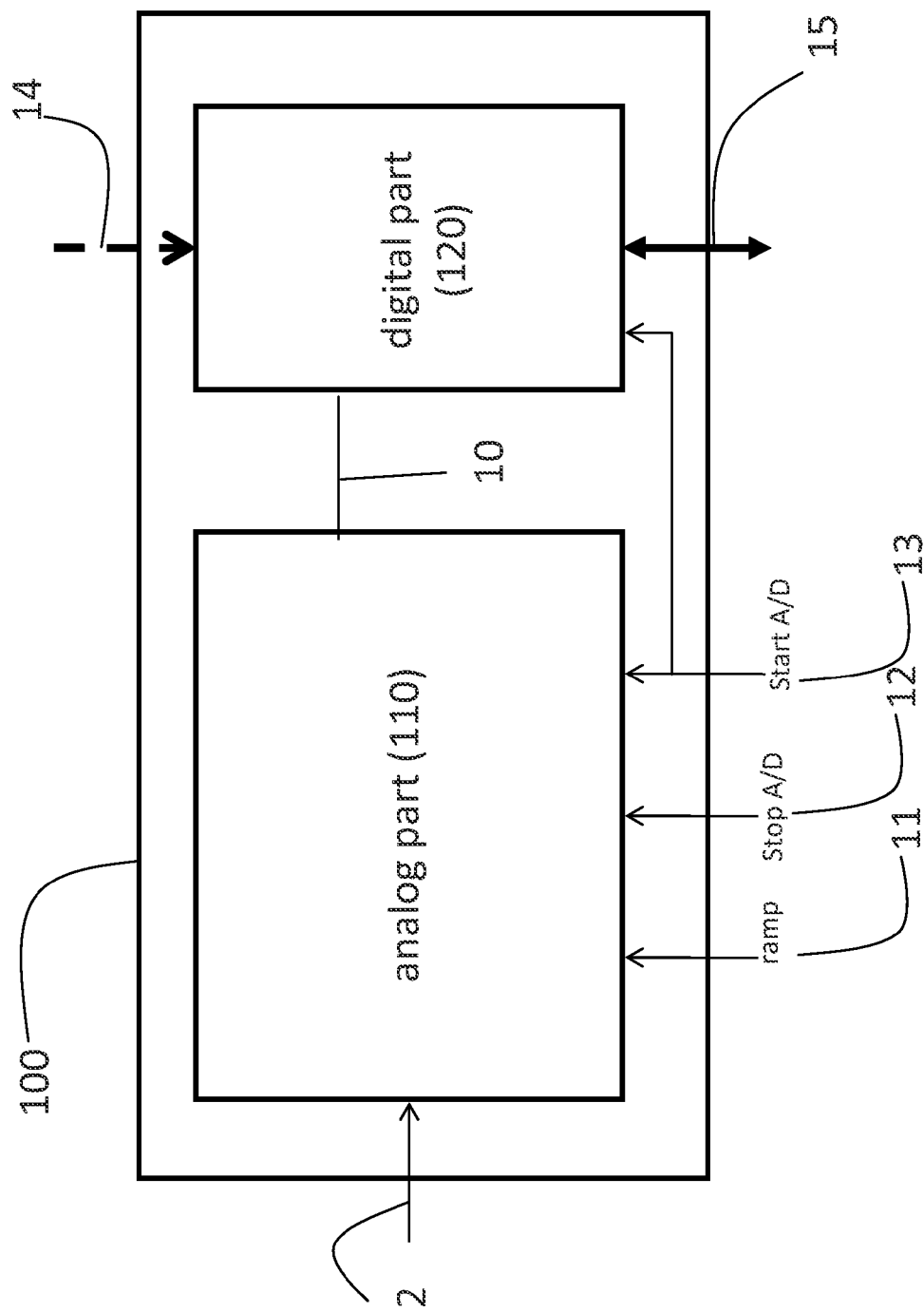
FIG. 1a presents a block diagram of a preferred pixel cell circuit according to the present invention.
Figure 1B:
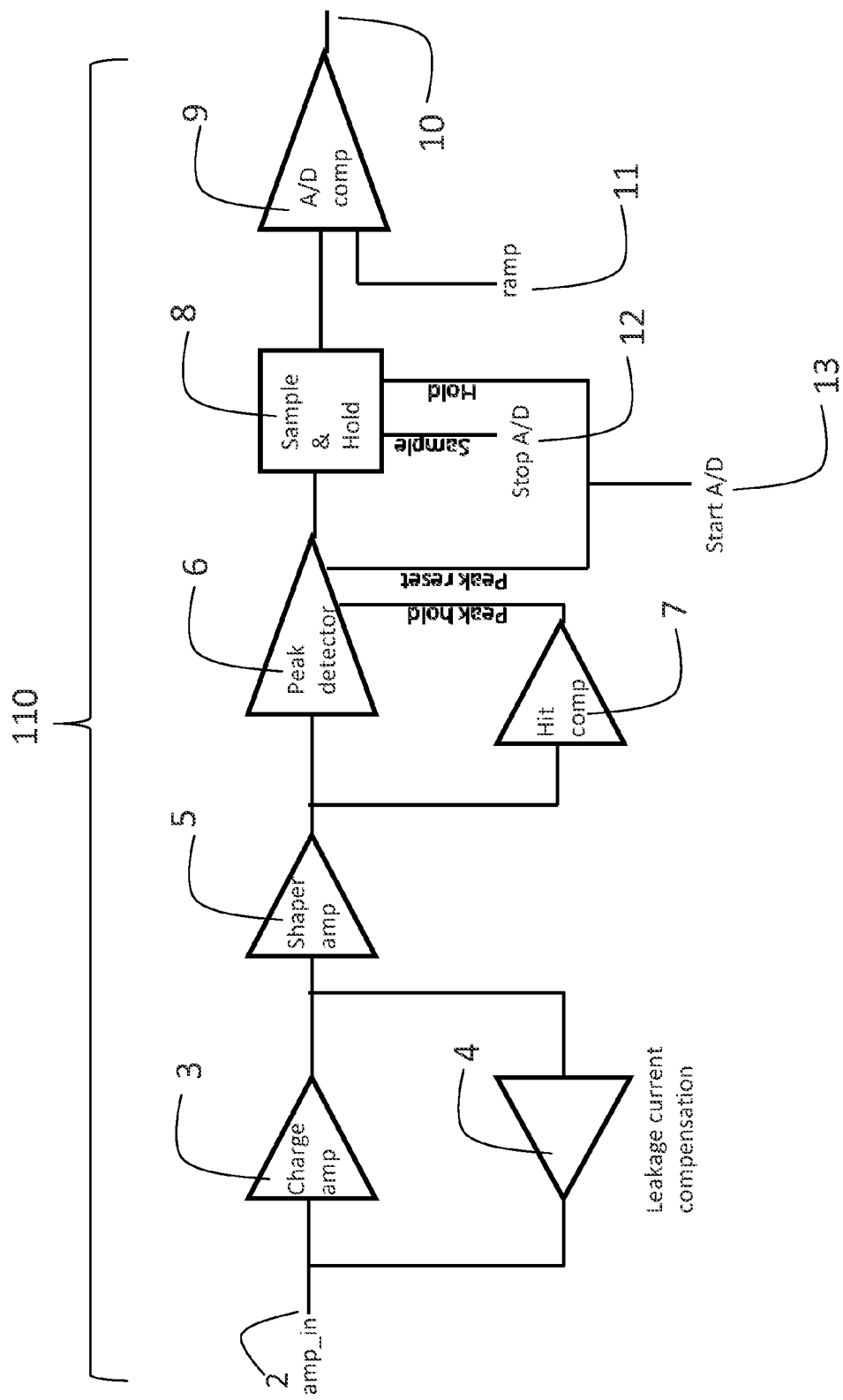
FIG. 1b schematically presents the analog part of the cell circuit.

A block diagram of the pixel cell circuit 100 of a preferred embodiment of the present invention is shown in FIG. 1a. Preferably there is one pixel cell circuit 100 associated with each detector pixel, but other embodiments are possible, for example several detector pixels corresponding to the same pixel cell circuit 100 or vice versa.

Figure 2:
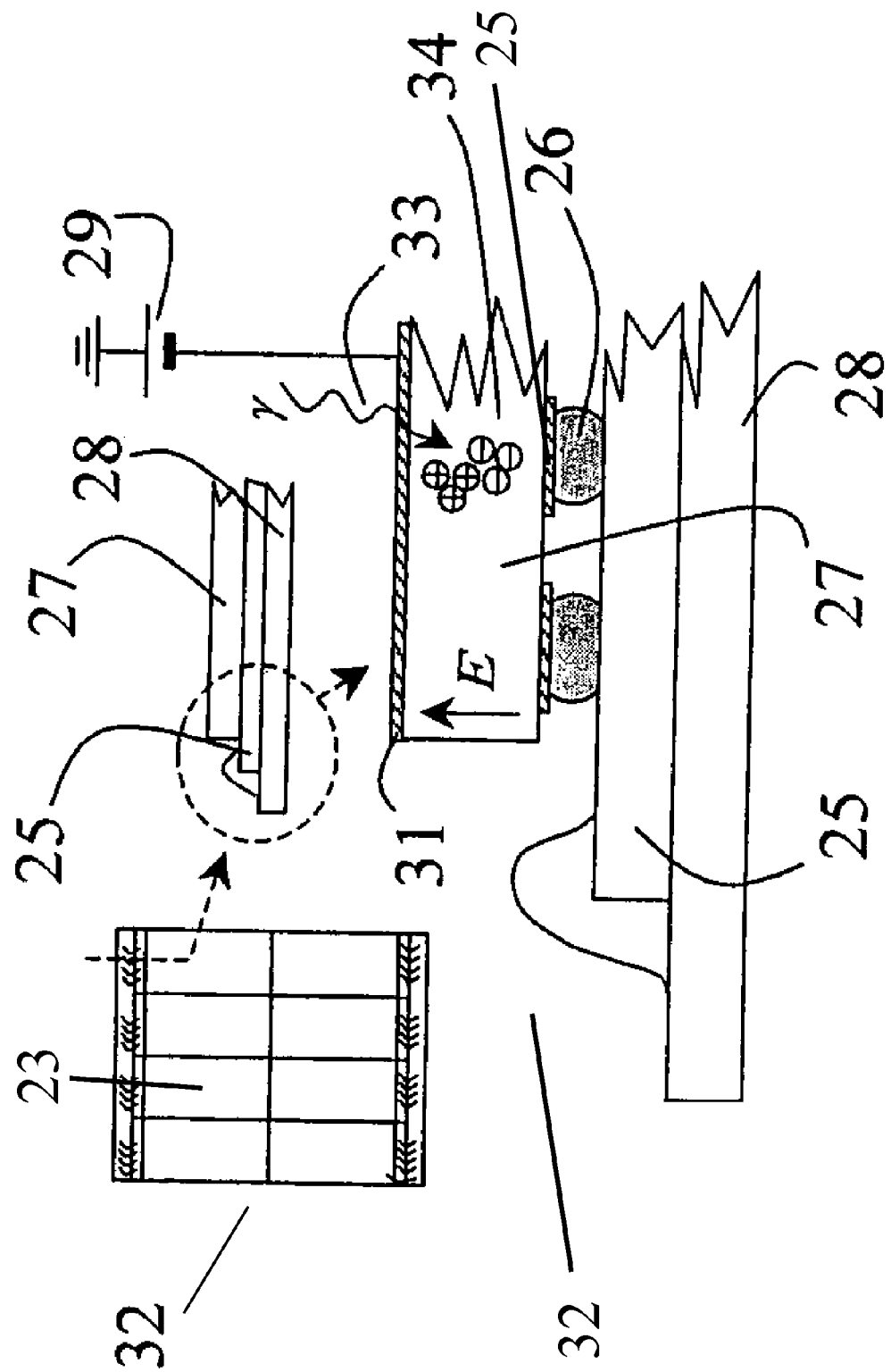
FIG. 2 shows schematically an imaging device comprising the CMOS circuit of the current invention bump bonded to a direct conversion detector substrate for detection and analysis of radiation quanta, i.e., x-ray and gamma ray photons or even charged radiation such as electrons, alpha particles, etc.

FIG. 2 shows an overview of the inventive radiation imaging device 32.

A radiation imaging detector 32 (an image sensor) is comprised of imaging cells 23, i.e., plural detector pixels implemented on detector substrate 27 and connected via bumpbonds 26 to the readout substrate 25. Other types of connection are possible such as using conductive epoxy, wire bonding or epitaxially growing the detector on the readout substrate. The readout substrate 25 is preferably CMOS circuit substrate, e.g., a substrate with a radiation identifying and processing application specific integrated circuit ("ASIC"). Other types of ASICs can be used or even other types of readout technologies such as Thin Film Transistor arrays ("TFT"). If a TFT is to be used then the detector is grown rather than mounted on the readout substrate. The plural imaging cells 23 define a pixel array of radiation detector pixels. The readout substrate 25 provides plural pixel cell circuits 100 with each detector pixel connected to a corresponding pixel cell circuit via the bump bond 26. Each pixel cell circuit 100 defines a readout pixel circuit. Each readout pixel circuit is coupled to a corresponding one of the radiation detector pixels (however without departing from the scope of the invention multiple radiation detector cells can be connected to the same pixel cell circuit 100 or vice versa.

Thus, with reference to FIGS. 1-2, the invention includes a radiation imaging device 32 having the detector substrate 27 connected to the readout substrate 25.

The radiation imaging device 32 comprises the image sensor 32 connected to the readout substrate 25, which is a CMOS circuits substrate, e.g., a substrate with a radiation identifying and processing ASIC.

Image sensor 32 is comprised of plural imaging cells 23, which imaging cells 23 may also be called detector pixels. The image sensor 32 may also be called a radiation detector or radiation imaging detector.

In one preferred embodiment, the detector 32 includes a plurality of individual imaging cells 23 within detector substrate 27, each imaging cell 23 generating a charge 34 in response to incident radiation 33 events and outputting the generated charge 34 at an imaging cell output 35 via bumpbonds 26. A capacitor 29 is provided between layer 31 and ground. Arrow E represents electron flow towards layer 31. The application specific integrated circuit provides the pixel cell circuits 100. The application specific integrated circuit, located on readout substrate 25, includes individually a different pixel cell circuit 100 connected respectively to a corresponding one of the imaging cell outputs 35, each pixel circuit 100 receiving and processing the generated charge 34 received from the corresponding one imaging cell output 35, via, e.g., bump bond 26.

Referring to FIG. 1a, each pixel circuit 100 includes an analog part 110 and a digital part 120. The analog part 110 is presented in FIG. 1b. The analog part includes a charge amplifier 3 with detector leakage current compensation circuit 4, a shaper amplifier 5, a peak detector 6, a comparator producing a hit flag 7, a sample and hold circuit 8 and an Analog to Digital ("A/D") conversion comparator 9. The pixel circuit is connected to a corresponding semiconductor detector pixel cell at the input 2 of the charge amplifier 3. The output of the charge amplifier 3 is connected to the input of the shaper amplifier 5, while the leakage current compensation circuit 4 monitors the direct current ("dc") level of the output of the charge amplifier 3 and cancels as much leakage (or dark) current (i.e., current not created from incoming radiation) coming to its input 2 from the detector substrate 27 as needed in order to keep this dc voltage level equal to the one with zero detector leakage current. The output of the shaper amplifier 5 is connected to the input of the peak detector circuit 6 and to the comparator 7. The peak detector circuit 6 detects and stores the analog amplitude maximum appearing at the shaper 5 output. The hit flag comparator 7 compares the shaper 5 output to a predetermined voltage level placed above the dc baseline level of the shaper 5 and produces a pulse which enables the peak detector 6 to store the analog amplitude maximum of the shaper 5.

The peak detector circuit is reset at the beginning of the Analog to Digital ("A/D") conversion period, after having placed the sample and hold circuit 8 at the hold mode. The peak detector circuit output 6 is connected to the input of the sample and hold circuit 8. Sample and hold circuit 8 is placed at the sample mode in the end of the A/D conversion period and, as said before, at the hold mode in the beginning of the A/D conversion period which coincides with the beginning of the next recorded frame period. The output of the sample and hold circuit 8 is connected to the one input of the A/D conversion comparator 9 while the other input is connected to a ramp generator (FIG. 3) whose output is common to all pixels.

Figure 1C:
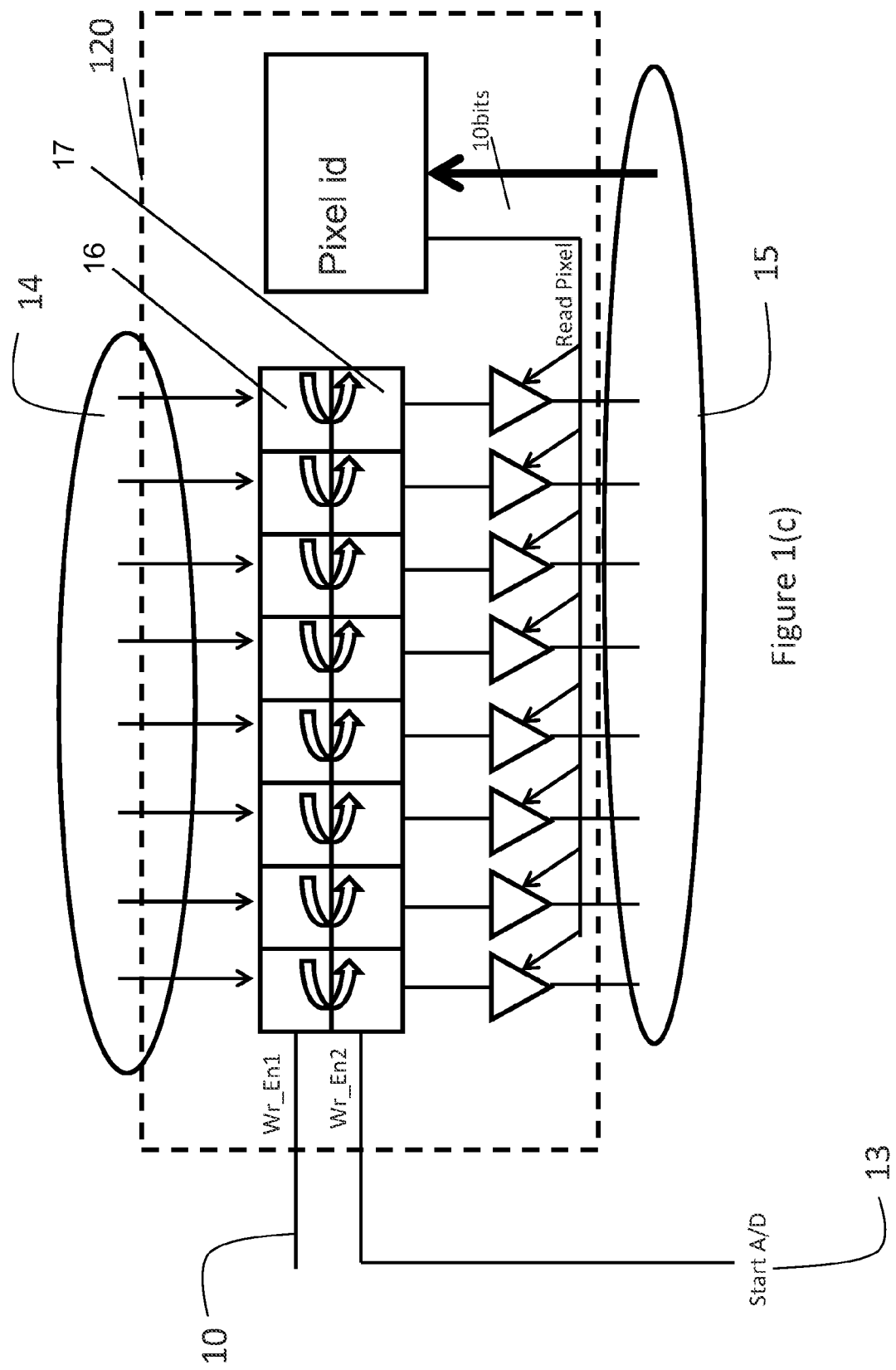
FIG. 1c schematically presents the digital part of the cell circuit.

The output of the A/D conversion comparator is connected to the write enable input 10 of a first memory 16 which is embedded in the digital part of the pixel cell circuit schematically depicted in FIG. 1c. The memory 16 receives input data words from an 8 bits Gray code counter 400 external to all the pixels which starts counting at the beginning of the A/D conversion phase and completes within 256 cycles. The counter could count more than 256 cycles if needed, thus increasing the number of bits to 10, 12 or even 14 bits. Thus, there are no in-pixel counters but there is instead a "global" counter external to all the pixels and peripheral on each CMOS ASIC (FIG. 3), such counter used for the digitization of the analog peak hold amplitude of each photon (x-ray event). The counter value is stored in the first memory when the ramp value exceeds the output of the sample and hold circuit. The stored digital word is transferred to a second memory 17 at the beginning of the next A/D cycle and the first memory 16 is ready to receive the result of the new A/D conversion. The word stored in the second memory 17 is transferred out of the pixel to the Digital Processing Unit 220 (FIG. 4) through the pixel I/O bus 15 (FIG. 3 and FIG. 4) when the pixel id (pixel identification) register receives through the same bus 15 a digital word (10 bits wide in the example embodiment) which is equal to its id (pixel identification), during the next integration frame period). The first and second memories 16, 17 together define a buffer for storing at least two values corresponding to the signal of at least two of the detected radiation events. The buffer may be any of an in-pixel digital buffer, in-pixel memory bank, an in-pixel DRAM, and an in-pixel analog buffer.

Figure 3:
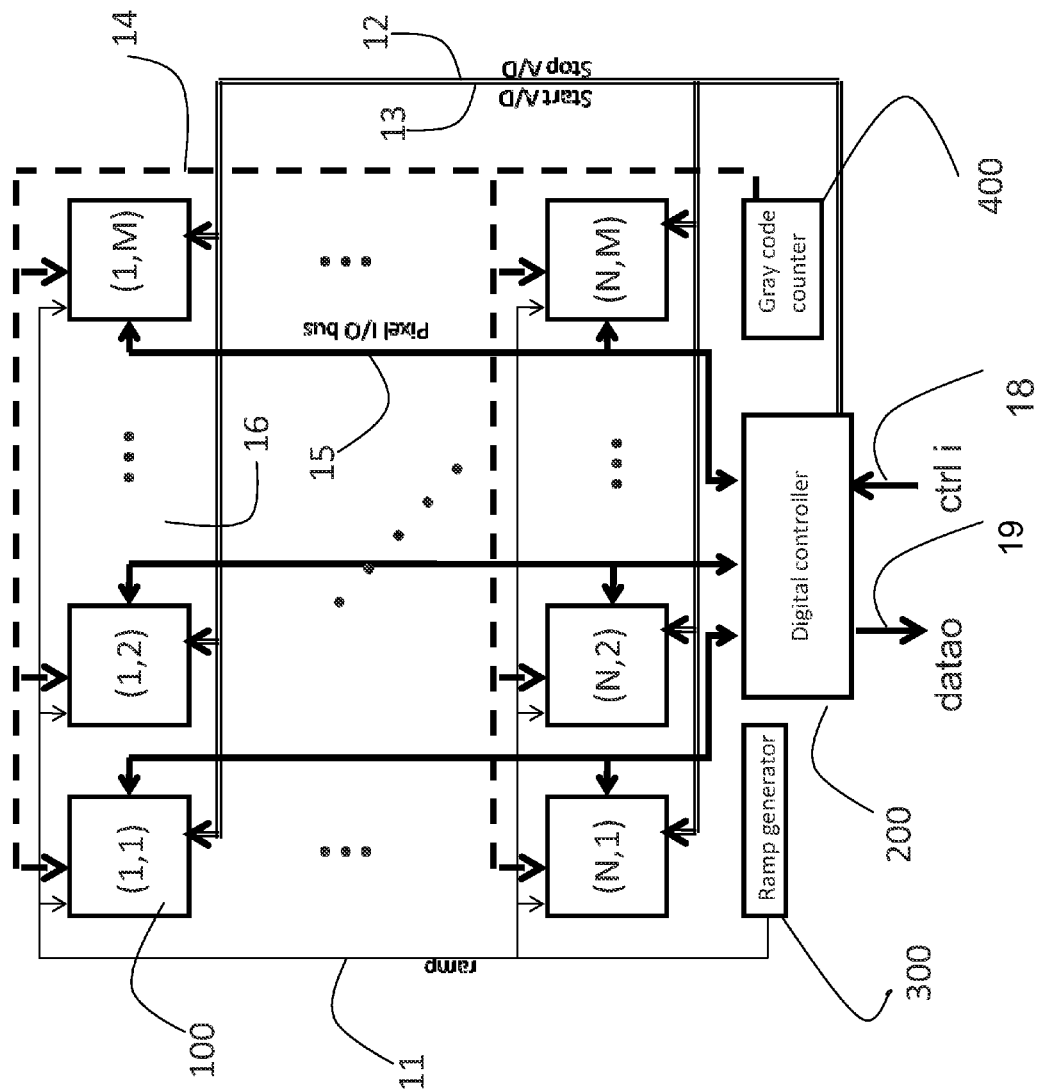
FIG. 3 shows an overview of the readout substrate including the M×N readout pixel circuits, the Analog to Digital Conversion ("ADC") unit and the digital controller. For the sake of clarity in this particular embodiment the ADC comprises several different circuit elements, namely the ramp generator 300, the gray code counter 400 and the A/D comparator 9. As can be seen the ramp generator 300 and the gray code counter 400 are both located off pixel (on the readout substrate) and the A/D comparator 9 is located on each pixel.

FIG. 3 gives an overview of the essential elements of the overall ASIC architecture. The N×M array of pixel cell circuits 100 receives input from a ramp generator 300, from a Gray code counter 400, and from an embedded digital controller circuit 200, all of these elements being outside the pixel array comprised of the imaging cells 23. The pixel array outputs the in-pixel stored data sequentially from all imaging cells 23 to the embedded digital controller, which is controlling the sequential readout from the pixel array and the transfer of the readout frames to the ASIC output. Thick lines 15 are the pixel output data path and signals that control the pixel memory readout, dashed thick lines 14 are the Gray code counter data words input to the first memory 16 of the pixel cell circuits 100. Thin line 11 is the output of the ramp generator transferred to all the pixel cell circuits 100. Time sequence signals are generated in the embedded digital controller of the ASIC and are transferred through lines 13 (Start A/D), 12 (Stop A/D) and 15 (Pixel I/O Bus) to all the pixel cell circuits 100.

In the example embodiment, N×M=250 rows×124 columns=31000 (pixels in said imaging device), Tint=10 µs (integration time for one photon or one radiation event), Tclk=10 ns (clock; transfer clock period).

Figure 4:
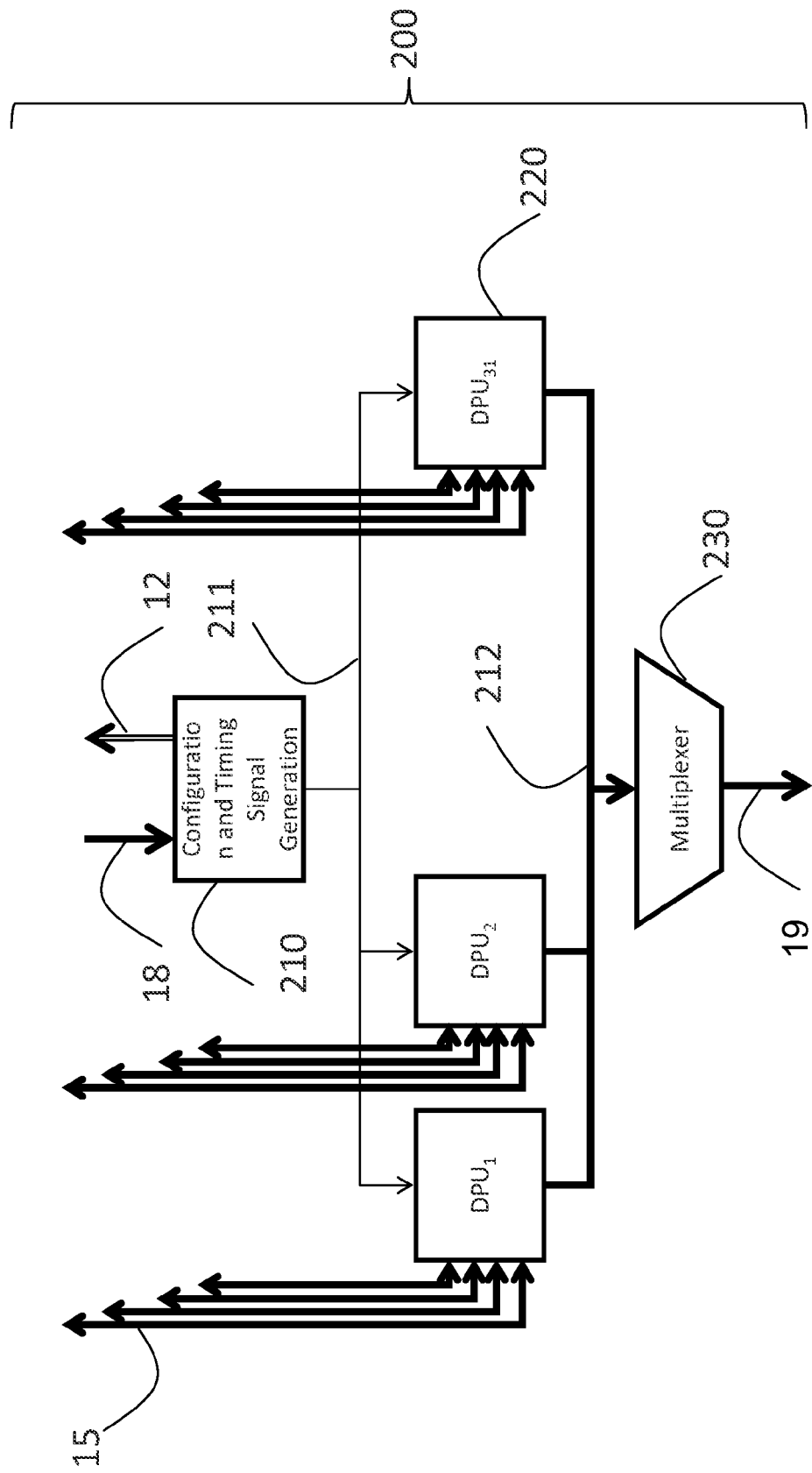
FIG. 4 shows a block diagram of the contents of the digital controller, including the Digital Processing Units ("DPU"s).

A block diagram of the off-pixel embedded digital controller circuit 200 of a preferred embodiment of the present invention is shown in FIG. 4. The embedded digital controller is generating all the timing signals for the control of the pixel array operation, sequential readout of the in-pixel stored data and output of the readout frames from the ASIC. The embedded digital controller is also implementing the input and output data interface of the ASIC. Thick line 19 is the embedded digital controller output where readout frames are transferred out of the ASIC. Thick control line 18 is the ASIC input receiving control signals for ASIC readout and configuration. The embedded digital controller comprises a control and timing signal generation unit 210, K Digital Processing Units (DPU) 220 and one data multiplexer 230. In the example embodiment of FIG. 4 the number K of DPUs is 31.

Figure 5A:
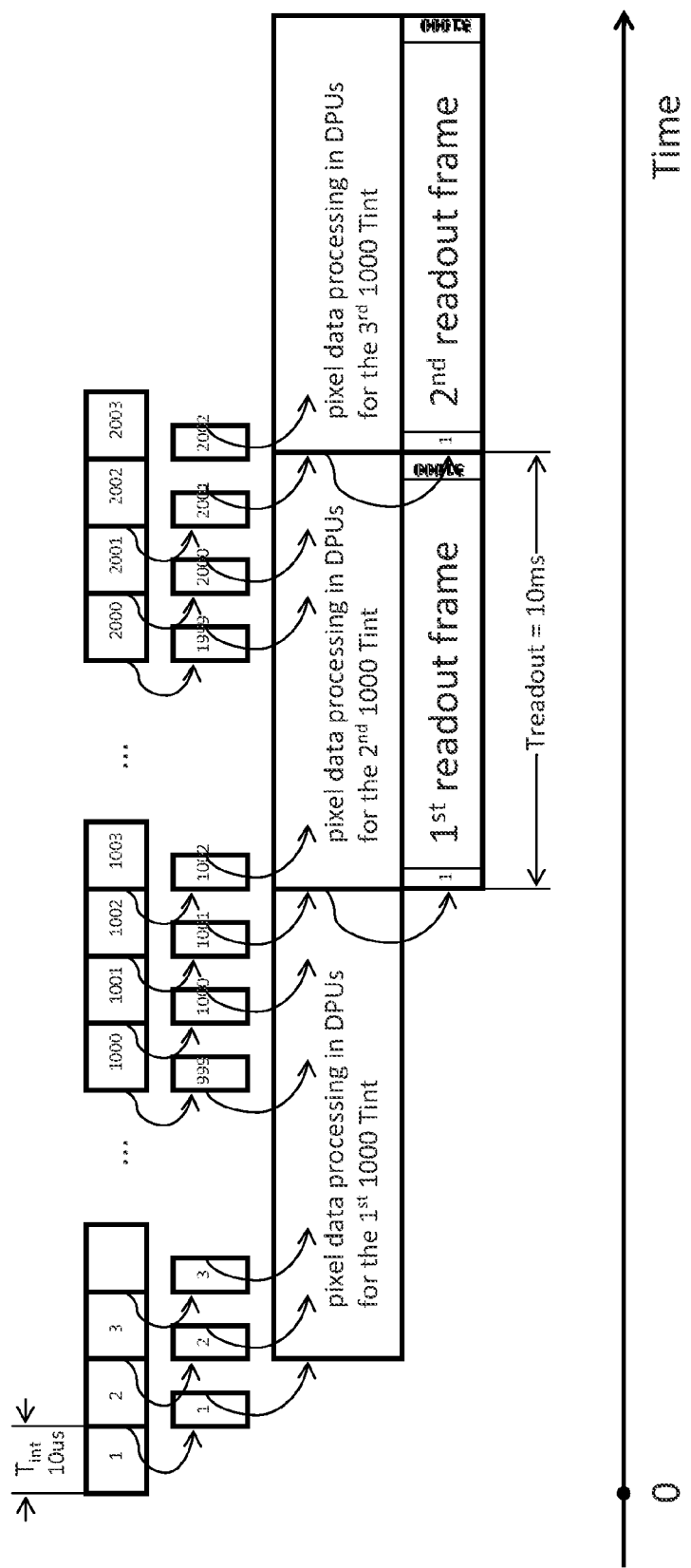
FIG. 5a shows a block diagram of how the pixel digital values are processed time wise into the DPUs, yielding readout frames.
Figure 5B:
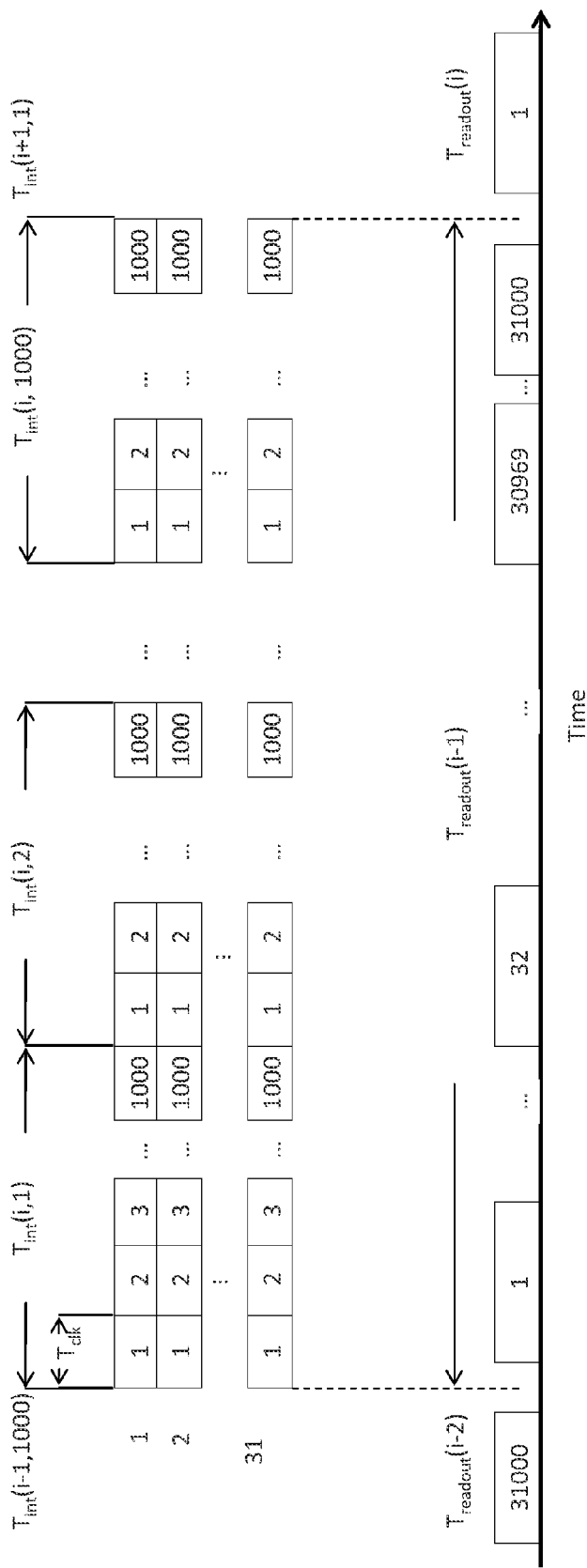
FIG. 5b shows the time wise data reduction using the DPUs and readout sequence.

The operating sequence in time of the ASIC is presented in FIGS. 5a and 5b. During the time interval Tint, called integration frame, the analog part 110 of the pixel cell circuit 100 records the charge induced by one x/gamma ray quantum, preferably the one with the highest induced charge. The A/D conversion period for the signal recorded during one integration frame starts at the beginning of the next integration frame and lasts for a time interval less than the integration frame. The digital value, which is the result of the A/D conversion, is stored within this interval in the first memory 16. In the example embodiment the integration frame Tint is 10 µs, corresponding to 100 kHz frame rate or 100,000 incident x-ray (or gamma ray) events per second per pixel. The transfer of the digital value, representative of the charge value (which in turn is representative of the energy of the incoming photon/radiation event) which is stored in the in-pixel memory, to the input of a Digital Processing Unit (DPU) 220, to which the pixel is connected via thick line 15, is done at the beginning of the next integration frame. Each transfer is done in Tclk which in the example embodiment is 10 ns. Consequently Tint/Tclk pixel digital values are transferred within one Tint interval (in the example embodiment 1000 pixel values) and for this reason K=(N×M)/(Tint/Tclk) Digital Processing Units (DPUs) operating in parallel are implemented in the embedded digital controller. In the example embodiment of FIG. 4 the number K of DPUs is 31. Each Digital Processing Unit (DPU) 220 is connected to the pixels of L=M/K=(Tint/Tclk)/N columns. In the example embodiment of FIG. 4 the number L of columns with pixels connected to DPUs 220 via thick lines 15 is 4. The operation sequence of the DPUs 220 is presented in more detail in FIG. 5b.

The data produced by the DPUs 220 are transferred out of the ASIC with period Treadout (defining the imaging device frame rate or frames per second), which is a multiple of Tint. In the specific embodiment presented here Treadout=1,000 Tint. The number of bits transferred out every Treadout is equal to the number of pixels multiplied by the number of bits enough to encode the decimal value of Treadout/Tint (in the example embodiment it is 10 bits). The information transferred out depends on the initial configuration setting of the ASIC which selects two different modes, mode 1 and mode 2.

In mode 1, the information transferred out is the number of hits recorded within the previous Treadout period with energy above a certain configurable threshold out of 256 for each pixel.

Figure 6:
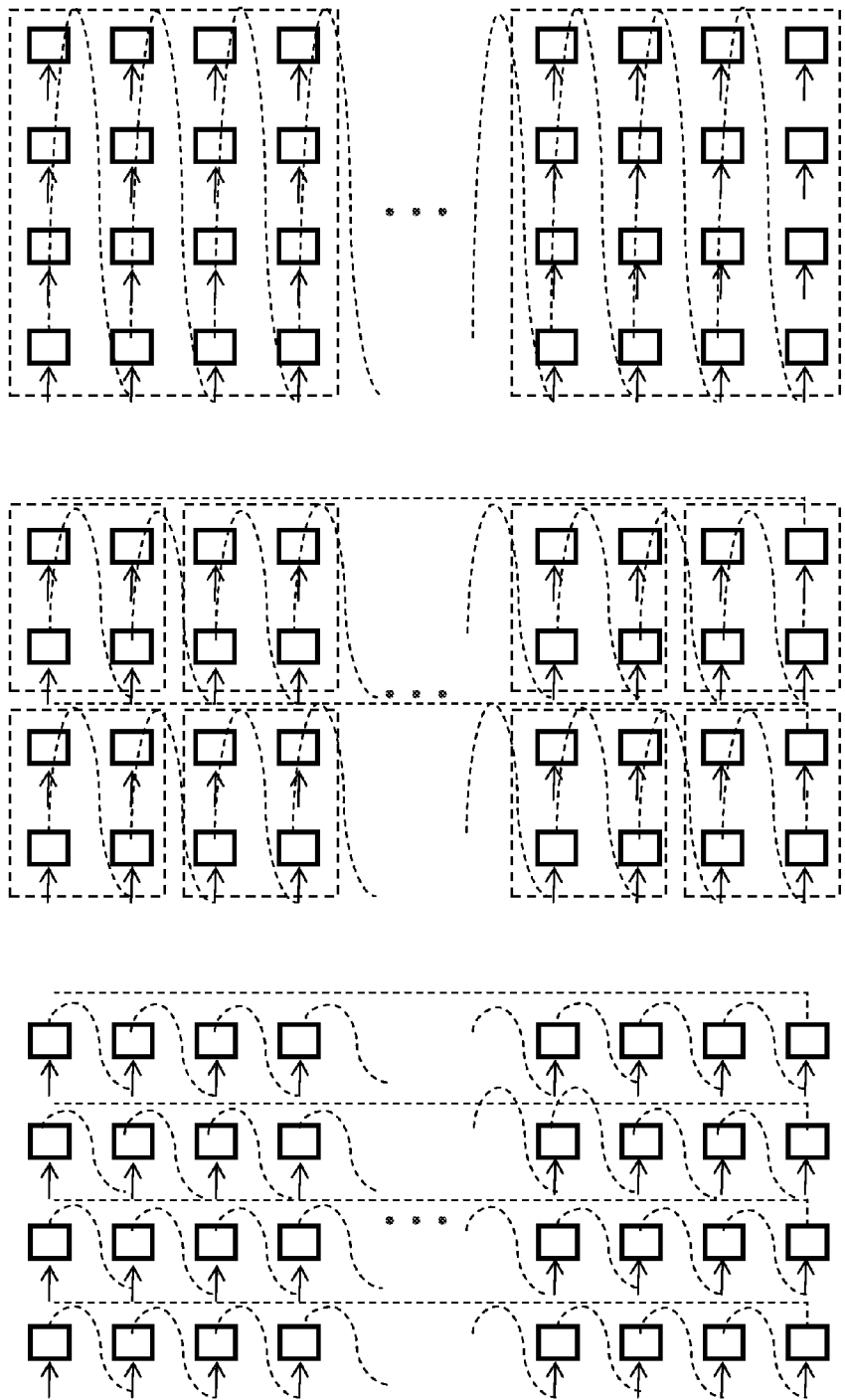
FIG. 6 shows the space wise (or spatial) data reduction by combining detector pixels to super pixels and the DPUs yield the number of photon events in M×N energy bins for M×N super pixels.

In mode 2, the same number of bits is used to transfer the number of hits recorded within the previous readout period with energies in each one of m bins, where now m=L×L and the hits belong to a "super-pixel", which comprises L×L neighbor pixels, for all "super-pixels". For the specific embodiment two kinds of "super-pixels" are foreseen: One made of 2×2 pixels resulting to energy bins and another made of 4×4 pixels resulting to 16 energy bins. The sequence of transfers of the digital values from each in-pixel memory to the input of the Digital Processing Unit (DPU) 220 for each mode of operation is shown in FIG. 6.

Figure 7:
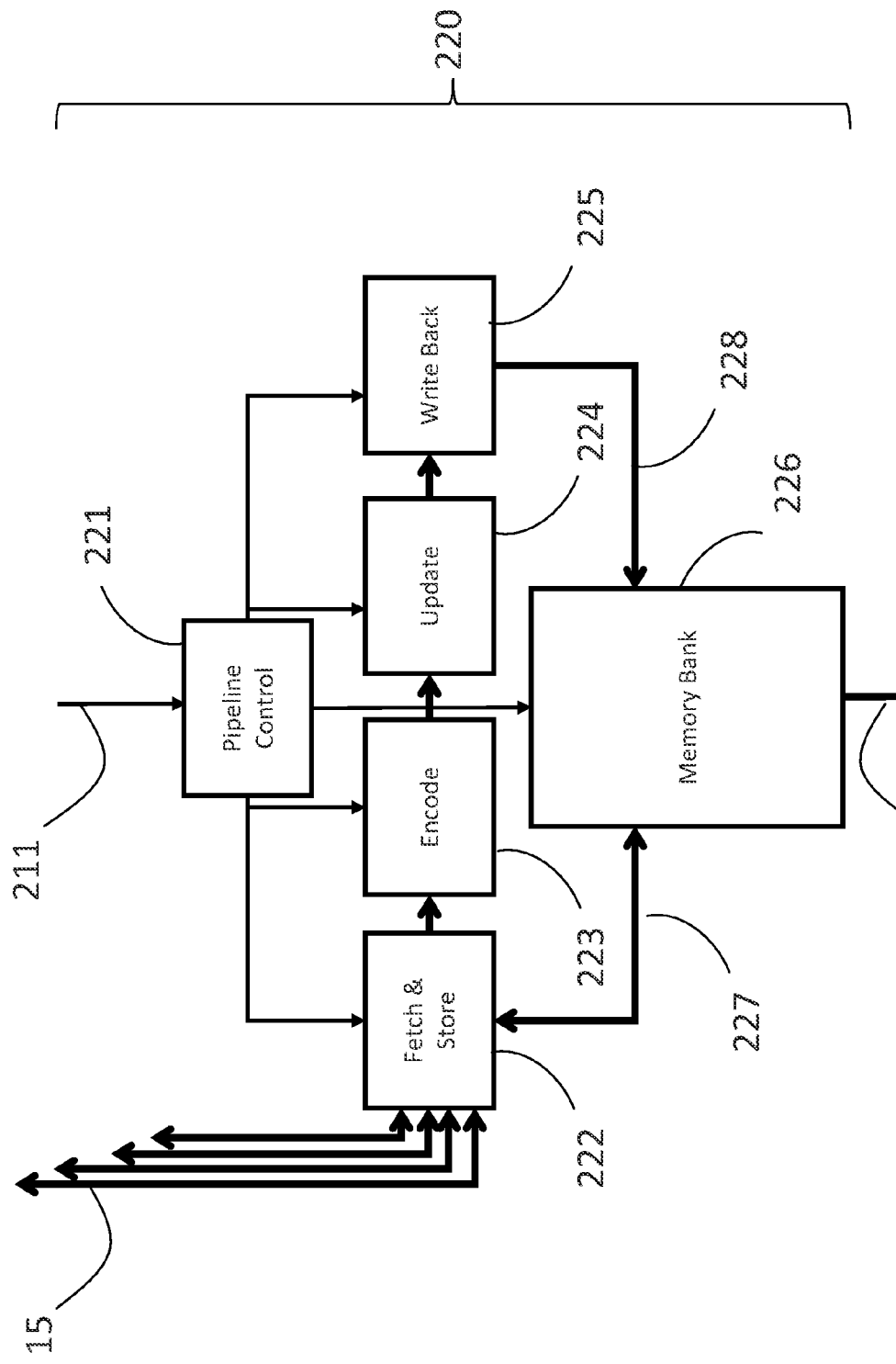
FIG. 7 shows further details of the digital controller, specifically the Digital Processing Unit(s) ("DPU") 220 including the memory bank (or buffer) and other elements.

A block diagram of a preferred embodiment of the DPU 220 is shown in FIG. 7. Each DPU 220 comprises a Pipeline Control unit 221, a Fetch & Store unit 222, an Encode unit 223, an update unit 224, a Write Back unit 225, and a Memory Bank 226.

Each DPU 220 performs one transfer operation every Tclk from the Tint/Tclk pixels sequentially. The sequence of transfers presented in FIG. 6 is controlled by the Pipeline Control unit 221. The Pipeline Control unit 221 receives as inputs the configuration and timing signals from the Configuration and Timing Signal Generation unit 210 over line 211 and controls the sequence of memory access for transferring digital values from the in-pixel memories to the Fetch & Store unit 222 and from the Write Back unit 225 to the Memory Bank 226 every Tclk and from the Memory Bank 226 to the output bus 212 during the readout frame period.

The Fetch & Store unit 222 of the DPU 220 receives as inputs every Tclk interval the digital values from each second memory 17 which is accessed in this Tclk interval, over thick lines 15 and the corresponding bin level stored during the previous Tint in the local Memory Bank 226 over thick line 227 (an old bin level).

In mode 1, the Fetch & Store unit 222 delivers the pixel readout data and corresponding old bin level to the Encode unit 223 every Tclk. The Encode unit 223 compares the level of the pixel data with the configurable threshold and in case the pixel data is found higher than this a flag signal together with the old bin level is sent to Update unit 224. In case of presence of the flag signal the Update unit 224 increases the bin level by one and transfers the new value (a new bin level) to the Write Back unit 225, which then writes the new bin level value to that position in the local Memory Bank 226 which corresponds to the readout pixel over thick line 228.

In mode 2, the Fetch & Store unit 222 every Tclk adds the pixel readout data to the value of a local counter and stores locally the corresponding bin level of the previous Tint, which is read from the local Memory Bank 226. Every L×L×Tclk a super-pixel readout is completed and then the value of the counter is transferred to the Encode unit 223 together with the L×L old bin level values and the Fetch & Store unit 222 resets the local counter in the following Tclk interval. The Encode unit 223 after a complete super-pixel readout encodes the counter value received from the Fetch & Store unit 222 to one of the m bins and transfers the encoded value together with the old L×L bin level values to the Update unit 224. The Update unit 224 increases the old bin level value of that bin level which corresponds to the encoded value by one and transfers the new bin level value to the Write Back unit 225 together with the encoded value. The Write Back unit 225 then writes the new bin level value to that position in the local Memory Bank 226 which corresponds to the readout super-pixel and the encoded value over thick line 228.

After each Treadout period the bin level values that have been stored in the Memory Bank 226 of each DPU 220 during this period are sent to the output over bus 212 during the following Treadout period. The Configuration and Timing Signal Generation unit 221 transfers the data from the local Memory Bank 226 of each DPU 220 sequentially as shown in FIG. 5b over the output bus 212 to the output Multiplexer 230 and then to the ASIC output over the output data bus line 19.

The configuration of the ASIC mode of operation is done through the transfer of appropriate control signals over the control line 18 to the embedded digital controller 200. The mode of operation of all Digital Processing Units (DPUs) 220 is then configured through thin line 211. The configuration and timing signal generation unit 210 of the embedded digital controller 200 is generating the configuration and timing signals for the synchronization of the readout operation.

In a preferred embodiment the two modes of operation, i.e., the time wise and space wise data reduction is provided simultaneously. For example for each frame one preferably receives the number of photon events above a certain threshold for each physical (or detector pixel during the frame integration time and at the same time the M×N energy bins with the number of photon events in each energy bin for each super pixel comprising the M×N pixel grouping. Furthermore in some other embodiments some of the frames may contain only the number of photon events in each pixel above a threshold and some of the frames may contain additionally the number of photon events in each energy bin for each super pixel comprising the M×N pixel grouping.

It is the therefore understood that in accordance with the current invention, one is able to achieve a list of critical aspects for imaging summarized here:

Energy identification for each x-ray, gamma ray or other type of radiation, with increased energy resolution.

A count rate of incoming radiation of 100,000 events per pixel per second or more and even up to 1,000,000 events per pixel per second, rendering this imaging device suitable for most medical, dental and industrial x-ray (gamma ray) imaging applications The ability to identify the energy of each incoming x-ray at these high rates, allows energy dispersive imaging which yield higher contrast resolution and diagnostic ability, including colorization of soft and bone tissue in medical and dental applications.

Fast Image frame rate (100 fps in the above example)

There is practically no inactive time while producing and reading out the image frames, There are no in-pixel counters (i.e., no counters for counting x-ray events within pixel cell circuits 100), which means that power consumption is greatly reduced while energy resolution and number of energy bins per radiation event is improved A global (for the whole ASIC) counter can be used to digitize the analog charge amplitude for each pixel and each event. This counter is used as an Analog to Digital Converter and NOT as a counter for counting photons.

In a photon identifying imaging device a digital controller residing on the readout substrate and preferably off-pixel, has the functionality of reducing the data time wise, spatial wise or both. While the integration time in the exemplifying embodiment is 10 usec (ten micro seconds), the readout time (or frame time) is 1,000 slower or 10 msec (ten milliseconds). In this way, a great reduction of the data is achieved in time. On the other hand, the invention provides the number of incident photons above a threshold for every pixel or four energy bins for 2×2 "super" pixels or nine energy bins for 3×3 "super" pixels or sixteen energy bins for 4×4 "super" pixels and so on. The "super" pixels need not be symmetric; for example they could be 1×2, 2×3 or any combination of the individual pixels. This versatility and flexibility offers unique opportunities in imaging and combines the best features of energy dispersive imaging with sufficient energy resolution (number of energy bins), without having in-pixel any photon counting counters.

Although specific embodiments have been described to exemplify the current invention, someone skilled can accommodate additional embodiments and variations without departing from the scope of this invention. For example, the detector material is preferably CdTe or CdZnTe which is a direct convertor with high sensitivity (detector substrate 27 in FIG. 2). However, other direct conversion materials can be used; for example Ge, GaAs, PbI, HgI etc. Additionally, the readout ASIC was described to be preferably a CMOS, but other types of readout circuits can be used such as BiCMOS or Thin Film Transistor arrays, without departing from the scope of the functionality provided is as described herein. Also the detector material need not be a direct convertor, but could be a scintillator or phosphor which converts x-rays and gamma rays to light and then light converts to an electronic signal at the CMOS. Such indirect conversion materials could be for example NaI, CsI etc.

The integration times and clock frequencies presented here, exemplify a practical implementation of the current invention but other integration times per single frame and master clock frequencies can be used. Typical integration times may vary from one microsecond to about a second and typical master clocks (for the clocking for example of the digital values from the in pixel memory banks) from 1 nsec (nanno second) upwards.

The energy of the incoming radiation is typically high as is commonly used in radiation imaging applications and varies from about 1 keV to more than 500 Mev. For most dental, medical and industrial applications the x-ray and gamma ray photons are in the range of 10 keV to 300 keV. Although the current invention is particularly useful for x-ray and gamma ray imaging applications in the above energy range, it is also useful for other types of radiation such as charged radiation, for example beta and alpha radiation.

Also the notion of "detector pixel(s)" coupled to "readout circuit pixels" should be understood as the imaging element producing after processing pixel values in an image to be displayed, whether the actual detector pixel is defined by lithography on a semiconductor substrate or by means of coupling a certain part of a scintilator substrate (or phosphor) to an individual readout circuit. Also in the case of 3D or CT imaging the detector pixel and readout circuit pixel coupled to the detector pixel is an imaging element producing the data that after processing (at a computer or otherwise) lead a 3D data set or otherwise known as voxel data set.

The preferred embodiments described herein comprise a digital in-pixel buffer, for example a bank memory such as a DRAM. This approach is optimal both in terms of speed and power consumption. However, if the event rates are not as demanding one can implement on each pixel also analog buffers. Although power consumption is expected in general in this case to be higher, such analog buffers could handle low to moderate event rates, for example from few to 10,000 events per pixel per second. With digital in-pixel buffers and the taught technique of a digital on-chip (but off pixel) controller including DPUs that execute time wise and space wise data reduction, one handle events rates up 100,000 events per pixel per second and even higher up to 1,000,000 events per pixel per second.

The invention claimed is:

1. A photon/energy identifying radiation imaging device comprising:
    a detector substrate having a two dimensional array of radiation detector pixels for detecting incoming radiation events that allows for a count rate determination, in events per pixel per second, of incoming individual radiation events and to identify an energy of each incoming radiation event, said radiation detector pixels convert each incoming radiation event into a single-photon electrical signal; and
    a readout substrate comprising a two dimensional array of readout pixel circuits coupled to said radiation detector pixels for processing electrical signals respectively corresponding to the single-photon electrical signal of each said incoming radiation events, wherein said readout substrate further comprises both of:
        a peak detector circuit to detect the peak value of a single-photon electrical signal, a sample and hold circuit to sample and hold said peak value and an Analog to Digital Conversion stage for digitizing said peak value of said single-photon electrical signals from individual incident photon events into digital values of the peak of the single photon signal respectively representing values of the energy of the detected individual radiation events, and
        a digital controller for receiving said digital signal values and further processing the received digital signal values prior to readout,
    wherein each of said incoming radiation events is an individual radiation photon from the group consisting of at least one of x-rays and gamma rays.

2. A photon/energy identifying radiation imaging device according to claim 1, wherein,
    more than half of said readout pixel circuits further comprise a buffer for storing at least two values corresponding respectively to the single-photon electrical signal of at least two individual detected radiation events, the two values respectively representing values of the energy of the individual detected radiation event for that pixel for each of the two individual detected radiation events.

3. A photon/energy identifying radiation imaging device according to claim 2, wherein,
    said two dimensional array of radiation detector pixels allows detection of a count rate of incoming individual radiation in a range from a few events per pixel per second to 1,000,000 events per pixel per second, and allows the identification of the energy of each incoming radiation event over said range,
    said readout substrate is a unitary readout substrate comprising all of said readout pixel circuits and each of said buffer, and
    said buffer is an in-pixel digital buffer.

4. A photon/energy identifying radiation imaging device according to claim 3, said two dimensional array of radiation detector pixels allows detection of the count rate of incoming individual radiation in a range from 10,000 events per pixel per second to 1,000,000 events per pixel per second, and allows the identification of the energy of each incoming radiation event over said range, and
    wherein said digital buffer is an in-pixel memory bank.

5. A photon/energy identifying radiation imaging device according to claim 4, wherein said memory bank is an in-pixel DRAM.

6. A photon/energy identifying radiation imaging device according to claim 3, wherein said in-pixel digital buffer stores digital values, each digital value representing the energy of the individual detected radiation event for that pixel.

7. A photon/energy identifying radiation imaging device according to claim 3 wherein said readout substrate further comprises an analog to digital conversion circuit, the analog to digital conversion circuit for controlling execution of a analog to digital conversion process within each readout pixel circuit and for providing, as an output, resulting digital values of the amplitude of the signal of the detected radiation events.

8. A photon/energy identifying radiation imaging device according to claim 7, wherein said readout substrate further comprises an off-pixel counter.

9. A photon/energy identifying radiation imaging device according to claim 8, wherein said counter is a Gray code counter.

10. A photon/energy identifying radiation imaging device according to claim 2, wherein said buffer is an in-pixel analog buffer and said at least two values are analog or amplitude levels corresponding to at least two of the detected radiation events for that pixel.

11. A photon/energy identifying radiation imaging device according to claim 2, wherein said stored values on said in-pixel buffer are readout sequentially, under control of said digital controller circuit, for further processing.

12. A photon/energy identifying radiation imaging device according to claim 11, wherein the further processing is executed by a digital processing unit residing on some part of the readout substrate.

13. An energy identifying radiation imaging device according to claim 2, wherein said energy identifying radiation imaging device is a dental diagnostic imaging device.

14. A photon/energy identifying radiation device according to claim 1, wherein,
    said readout substrate is a unitary readout substrate comprising all of said readout pixel circuits, and
    said further processing comprises time wise data reduction, said time wise data reduction comprising providing the number of photon events incident on each pixel over a period of time and above a signal threshold, said period of time being a multiple of an integration time Tint for each photon event.

15. A photon/energy identifying radiation device according to claim 1, wherein,
    said readout substrate is a unitary readout substrate comprising all of said readout pixel circuits, and said further processing comprises space wise data reduction, said space wise data reduction comprising providing the number of photon events in each of M×N energy bins for each one of a super pixel, each super pixel comprising M×N detector pixels.

16. A photon/energy identifying radiation device according to claim 1, wherein said digital controller comprises a digital processing unit.

17. A photon/energy identifying radiation device according to claim 1, wherein said digital controller comprises a digital buffer or a memory bank.

18. A photon/energy identifying radiation device according to claim 1, wherein said detector substrate and said readout substrate are interconnected via bump-bonds, said bumps connecting detector pixels readout pixel circuits.

19. A photon/energy identifying radiation device according to claim 1, wherein said detector substrate comprises one of CdTe, CdZnTe, HgI, and PbI.

20. A photon/energy identifying radiation device according to claim 1, wherein said detector substrate comprises one of a scintillator and a phosphor.

21. A photon/energy identifying radiation device according to claim 1, wherein said readout substrate comprises a CMOS substrate.

22. A photon/energy identifying radiation device according to claim 1, wherein said readout substrate comprises a Thin Film Transistor array.

23. A photon/energy identifying radiation device according to claim 1, wherein said photon/energy identifying radiation device is a dental diagnostic imaging device.

* * * * *